(12) United States Patent
Ghaderi

(10) Patent No.: US 9,237,932 B2
(45) Date of Patent: Jan. 19, 2016

(54) VACUUM SHELL FOR ROBOTIC SURGERY OF SOFT TISSUE

(71) Applicant: Bahram Ghaderi, St. Charles, IL (US)

(72) Inventor: Bahram Ghaderi, St. Charles, IL (US)

( * ) Notice: Subject to any disclaimer, the term of this patent is extended or adjusted under 35 U.S.C. 154(b) by 19 days.

(21) Appl. No.: 14/171,935

(22) Filed: Feb. 4, 2014

(65) Prior Publication Data

US 2014/0228646 A1  Aug. 14, 2014

Related U.S. Application Data

(60) Provisional application No. 61/762,373, filed on Feb. 8, 2013.

(51) Int. Cl.
*A61B 19/00* (2006.01)
*A61B 17/00* (2006.01)

(52) U.S. Cl.
CPC .............. *A61B 19/2203* (2013.01); *A61B 17/00* (2013.01); *A61B 19/38* (2013.01); *A61B 2017/00796* (2013.01); *A61B 2019/205* (2013.01)

(58) Field of Classification Search
CPC .... A61B 19/2203; A61B 19/38; A61B 17/00; A61B 17/02; A61B 2017/00796; A61B 2019/205; A61M 1/0023
USPC ........... 600/37, 201, 205, 208, 210, 231, 235; 623/3.21; 128/897, 202.12; 606/119, 606/123, 191, 201
See application file for complete search history.

(56) References Cited

U.S. PATENT DOCUMENTS

| | | | |
|---|---|---|---|
| 5,701,917 A * | 12/1997 | Khouri | 128/897 |
| 6,042,539 A | 3/2000 | Harper et al. | |
| 6,146,377 A * | 11/2000 | Lee et al. | 606/13 |
| 6,558,314 B1 | 5/2003 | Adelman et al. | |
| 2003/0036677 A1 | 2/2003 | Taylor | |
| 2004/0073106 A1 * | 4/2004 | Lee et al. | 600/415 |
| 2010/0210915 A1 | 8/2010 | Caldwell et al. | |

* cited by examiner

*Primary Examiner* — Pedro Philogene
*Assistant Examiner* — David C Comstock
(74) *Attorney, Agent, or Firm* — Ice Miller LLP

(57) ABSTRACT

A device for assisting robotic surgery of soft tissue, that comprises a shell with a flexible sealing rim, instrument ports, and a vacuum port. The flexible sealing rim seals the shell around a surgical area and allows for the application of negative pressure via the vacuum port. The negative pressure manipulates soft tissue to allow a surgeon to perform an incision with a robotic surgery apparatus.

15 Claims, 6 Drawing Sheets

VACUUM SHELL FOR ROBOTIC SURGERY OF SOFT TISSUE

This application claims the benefit of U.S. provisional application Ser. No. 61/762,373, filed Feb. 8, 2013, which is hereby incorporated by reference in its entirety.

BACKGROUND OF THE INVENTION

The present invention relates to robotic surgery of soft tissue and, in particular, to devices for facilitating manipulation of soft tissues during surgical procedures.

Mastectomy, breast reduction, breast reconstruction and breast enhancement procedures have become commonplace. In typical surgical techniques for breast enhancement, a silicone or saline filled implant device is inserted into the breast after an incision in locations such as the inframammary fold, or periareolar area. In such procedures, it is often necessary for the surgeon to manipulate the soft tissue of the breast and hold it in place to allow easier access to the skin for a clean incision and placement of the breast implant. This minimizes scarring, provides better aesthetic appeal, and prevents post-surgical complications.

It is theoretically possible for robotic devices, such as those sold under the daVinci® trademark (Intuitive Surgical, Inc.—Sunnyvale, Calif.), to execute many breast enhancement procedures. However, it is difficult for a surgeon to operate a robotic surgery apparatus, and also to maintain soft tissues, such as breast tissue, in such a manner to provide the best incision as provided above. It would be desirable to have a device that could, in an automated way, allow manipulation of soft tissues in a surgical procedure.

SUMMARY OF THE INVENTION

A device is provided for expanding and manipulating soft tissue during surgery, that comprises a shell capable of withstanding negative pressure. The shell has a soft, flexible rim disposed around the peripheral edges of the shell for sealing to the skin of a patient to isolate a space between the shell and a surgical area. The shell also has one or more instrument ports for allowing resealable entry of surgical instruments, and a vacuum port that allows negative pressure to be applied to the space. The device is designed to be fit over the surgical area of operation to create a space around the surgical area, and with the vacuum port in communication with a vacuum pump so as to provide negative pressure to the surgical area through the shell in order to expand soft tissue to expose the skin to surgical instruments, and to assist in holding soft tissue in place.

In another embodiment of the invention, the vacuum port comprises a network of sealed slots disposed over the shell, that can be reclosably pierced by a vacuum hose assembly to slide along the slots move around on the surface of the shell. The vacuum hose assembly contains a sliding vacuum hose that can be extended or retracted into the shell to further provide localized negative pressure to soft tissue.

DETAILED DESCRIPTION OF THE INVENTION

Figure 1:
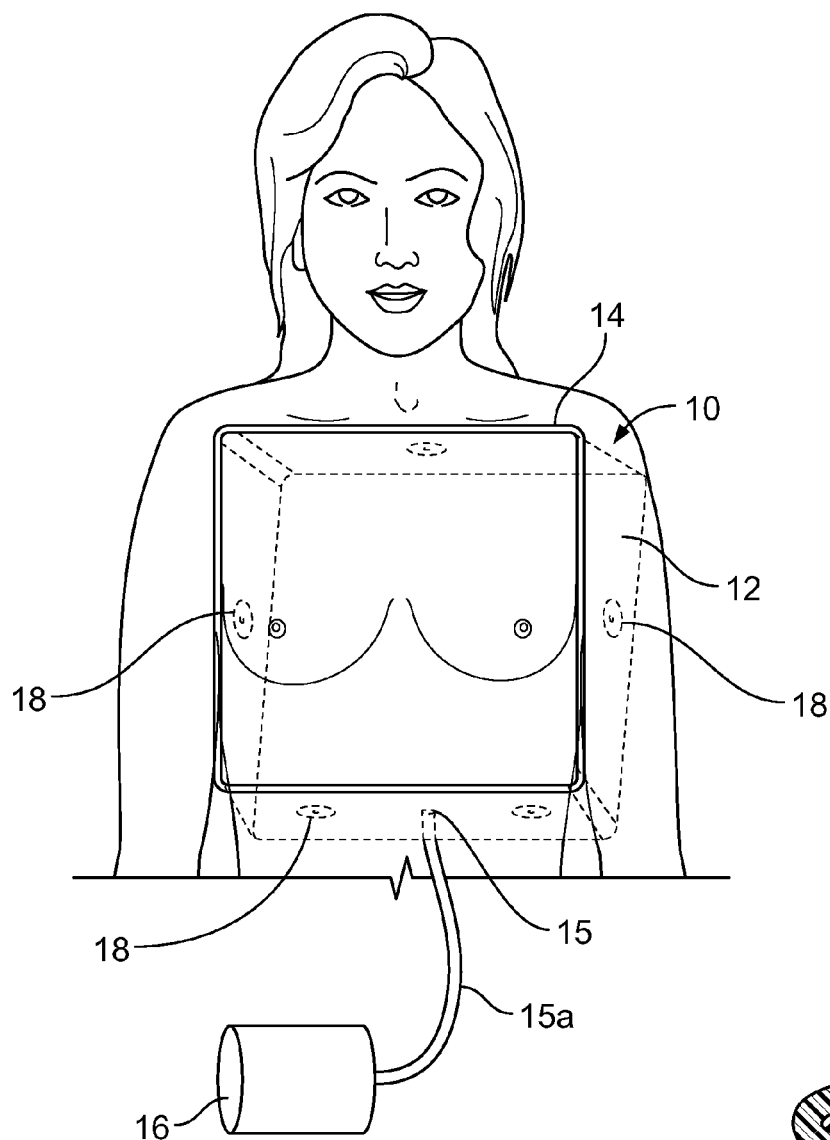
FIG. 1 is a front elevation view of a vacuum shell apparatus, showing how it would be mounted in a breast augmentation or other surgical procedure.

One embodiment of the soft tissue enlargement apparatus 10 may be generally comprised of an open shell 12 having a rim 14 and a vacuum port 15 which leads through vacuum hose 15a to a vacuum pump 16 for creating a vacuum within the shell 12. Although the vacuum pump assembly 16 may be a separate hand-held pump in one variant embodiment, in the preferred embodiment the vacuum pump assembly 16 is a self-contained vacuum pump with an independent power source, pressure sensor, and servomechanism for driving, regulating and controlling the vacuum pump 16.

The shell 12 may preferably be comprised of a rigid clear plastic material such as polycarbonate, which is sufficient to withstand vacuum pressure within the shell 12. Preferably, the shell 12 would be designed to fit over the chest area of a patient, and can be any shape, including a dome, to effect this purpose. Other specific embodiments of the shell may be configured to fit over a human breast, or as a bra shape.

The shell 12 may be designed to leave 1-5 inches of space between the area of operation and the shell, to provide space for tissue to expand, and sufficient space for surgical instruments to operate effectively. However, the shell 12 should not be so large so as to require a large pump to maintain sufficient negative pressure under the shell 12.

Figure 2:
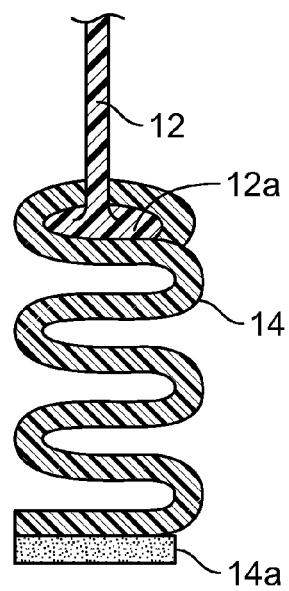
FIG. 2 is a side section, detail view of a rim portion of the vacuum shell apparatus of FIG. 1.

As shown in detail in FIGS. 1 and 2, The rim 14 may be a gasket disposed around the edges 12a of the shell 12, and may be comprised of a flexible, preferably soft material, such as rubber capable of forming a seal when contacted with skin. In the preferred embodiment, this rim 14 may be a silicone gel cushion or other soft, conforming type material. Petroleum jelly may also be used to supplement or supplant the rim. The rim 14 may be coated with a pressure sensitive adhesive material 14a, such as a double-sided adhesive with a peelable contact paper, to assist in maintaining sealing contact with the skin. The rim 14 may be sized to extend an inch or more from the edges 12a of the shell 12 in order to adapt to differing body profiles.

Regulation of the negative pressure within the shell 12 is essential to prevent contusions caused by rupturing capillaries adjacent the surface of the skin. Medical data suggest that these contusions will not occur if negative pressure within the shell is maintained at less than 20 mmHg. Thus, the vacuum pump 16 may be regulated to control the vacuum within the shell to within this limit. In addition, skin ulceration may occur if excessive contact pressures are applied thereto.

Medical data suggest that a negative pressure less than 20 mmHg may be applied indefinitely without such ulceration. However, contusions may occur due to positive contact pressures upon the skin at pressures above this ulceration limit.

The shell 12 may be provided with one or more sealing instrument ports 18 that are seals that can be reclosably penetrated by an instrument, such as an instrument driven by a robotic surgery device, such as a DaVinci surgical robot device. Such ports 18 may be formed by a circular disk of a flexible material such as a gel, having a pinhole at the center. The port 18 may be sealed against the environment, but may be expanded to fit around a surgical instrument when the pinhole is penetrated thereby. Other embodiments of sealed instrument ports may also be used.

In operation, the shell 12 may be placed over the surgical area, such as a chest area, such that the rim 14 is provides a seal with the patient's skin. The vacuum pump 16 may be used to provide negative pressure through port 15 and hose 15a. The negative pressure throughout the shell will allow the soft tissue of the breast to expand, and expose more of the skin to allow a clean incision and manipulation during surgery.

While the first embodiment allows for a constant negative pressure throughout the volume of the shell 12, it would be useful to modify the device so as to allow localized negative pressure, from the vacuum hose, at different points during surgery. For example, in a breast augmentation operation, the surgeon may want to provide concentrated negative pressure on the breast being operated on. A second specific embodiment is shown in FIGS. 3 and 4 showing one way to allow the surgeon to both provide negative pressure to the entire shell 12, and provide a concentration of negative pressure in a localized area by adjusting the placement of the vacuum port within the shell.

Figure 3:
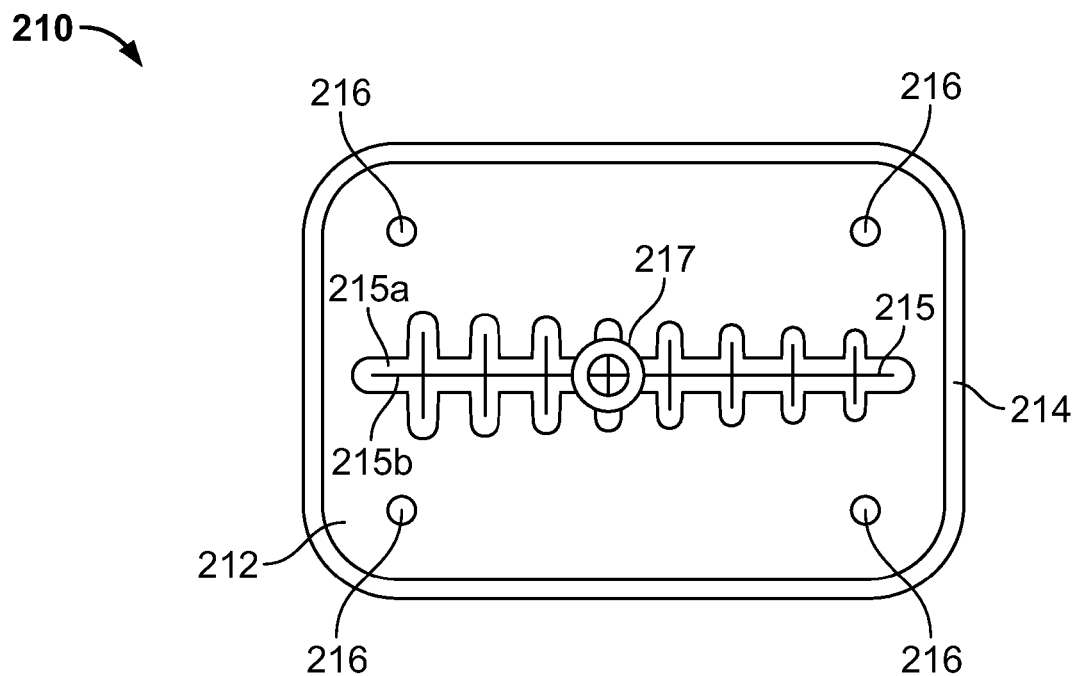
FIG. 3 is a top view of an alternative embodiment of a vacuum shell apparatus.

As seen in FIG. 3, a top view, a shell 212, similar to shell 12 in FIG. 1, may be designed to fit over the surgical area, in particular, the chest area for a breast enlargement procedure. The shell 212 may have a rim 214 essentially similar to the rim 14 described in FIG. 2, and one or more instrument ports 216 similar to instrument ports 18 disclosed in FIG. 1. The vacuum port 215, rather than being a single hole 15 as shown in FIG. 1, may be a slot or network of slots 215a in the shell that can allow a vacuum hose assembly 217 to travel at varying points across the shell 212. In the slots 215a of vacuum port 215, may be disposed a flexible sealing material, such as a gel, with a pin slit 215b extending lengthwise along all the slots forming the vacuum port 215. The pin slits, when not pierced by hose assembly 217, may be sealed by the expansion of the sealing material to allow negative pressure formation inside shell 212. The vacuum hose assembly 217 can be moved anywhere in the slots of vacuum port 215 to apply vacuum in a localized area.

Figure 4:
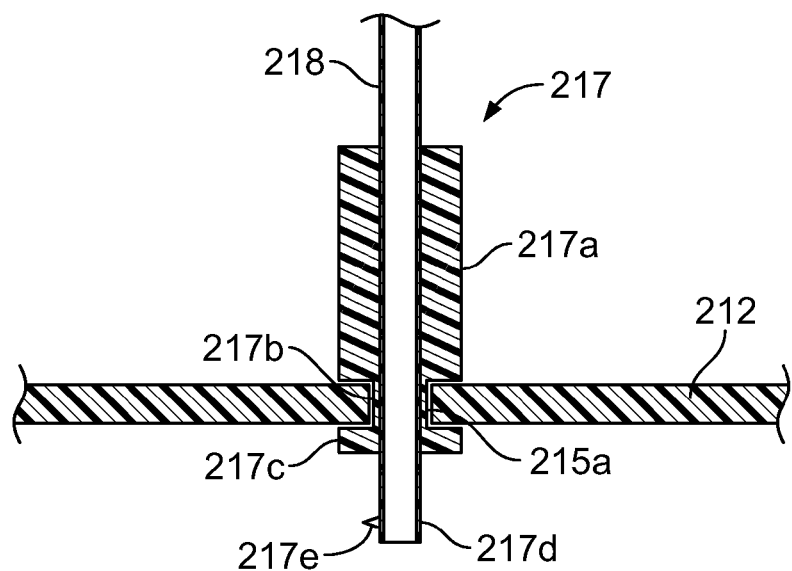
FIG. 4 is a side section, detail view of the embodiment of a vacuum shell apparatus of FIG. 3, showing the vacuum hose assembly.
Figure 5A:
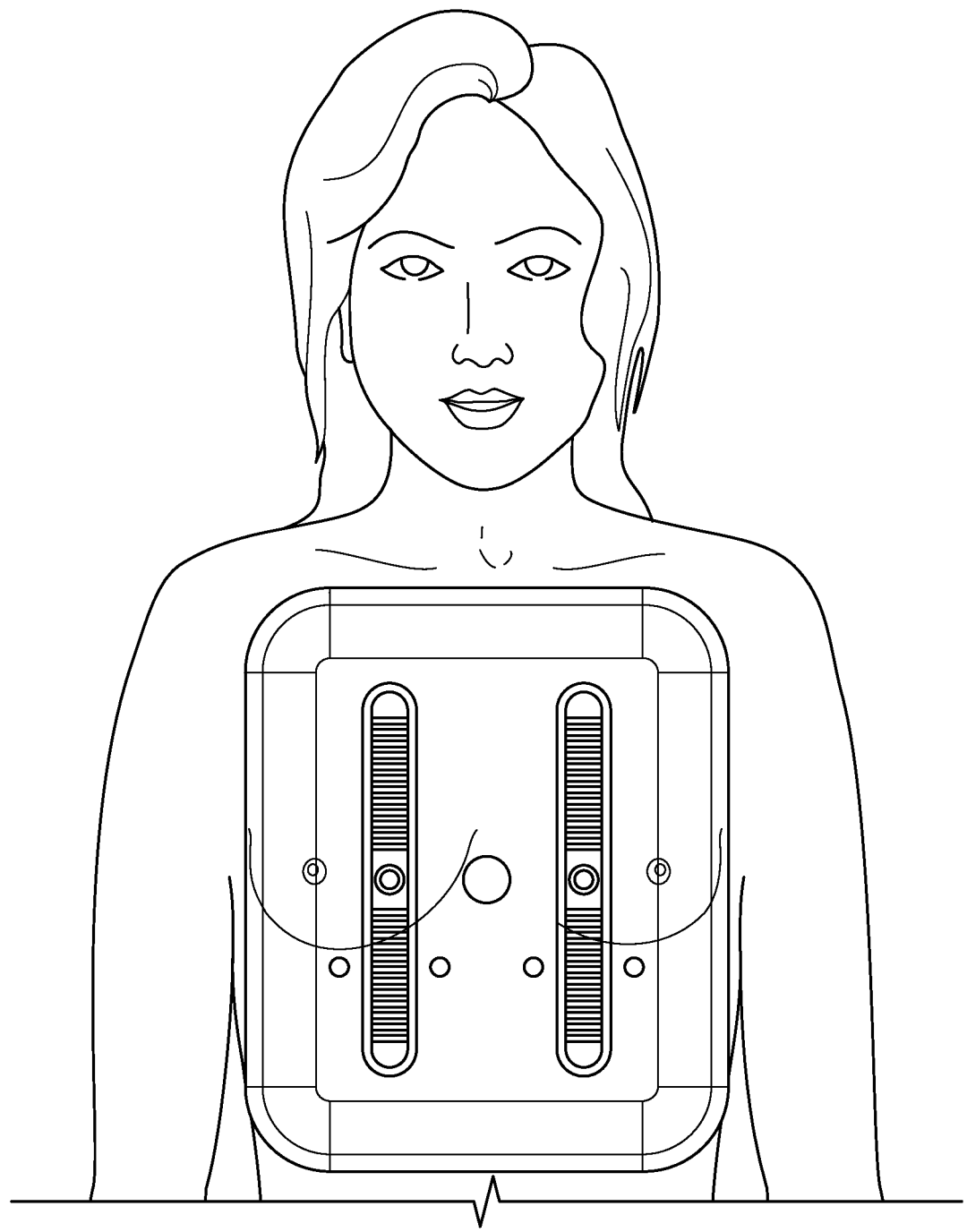
FIG. 5A is a front elevation view of yet another embodiment of a vacuum shell apparatus having moveable negative pressure points, showing how it would be mounted in a breast augmentation or other surgical procedure.
Figure 5B:
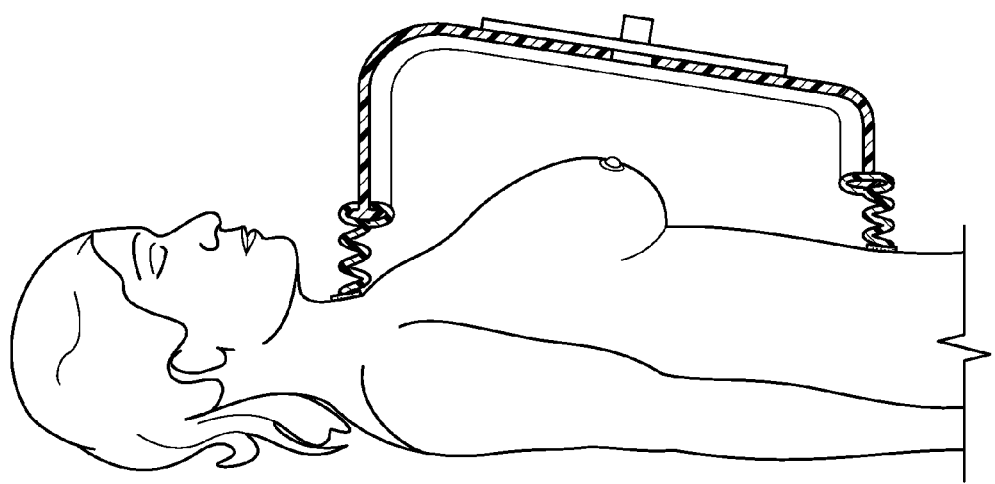
FIG. 5B is a side section view of the embodiment of a vacuum shell apparatus of FIG. 5A.
Figure 6:
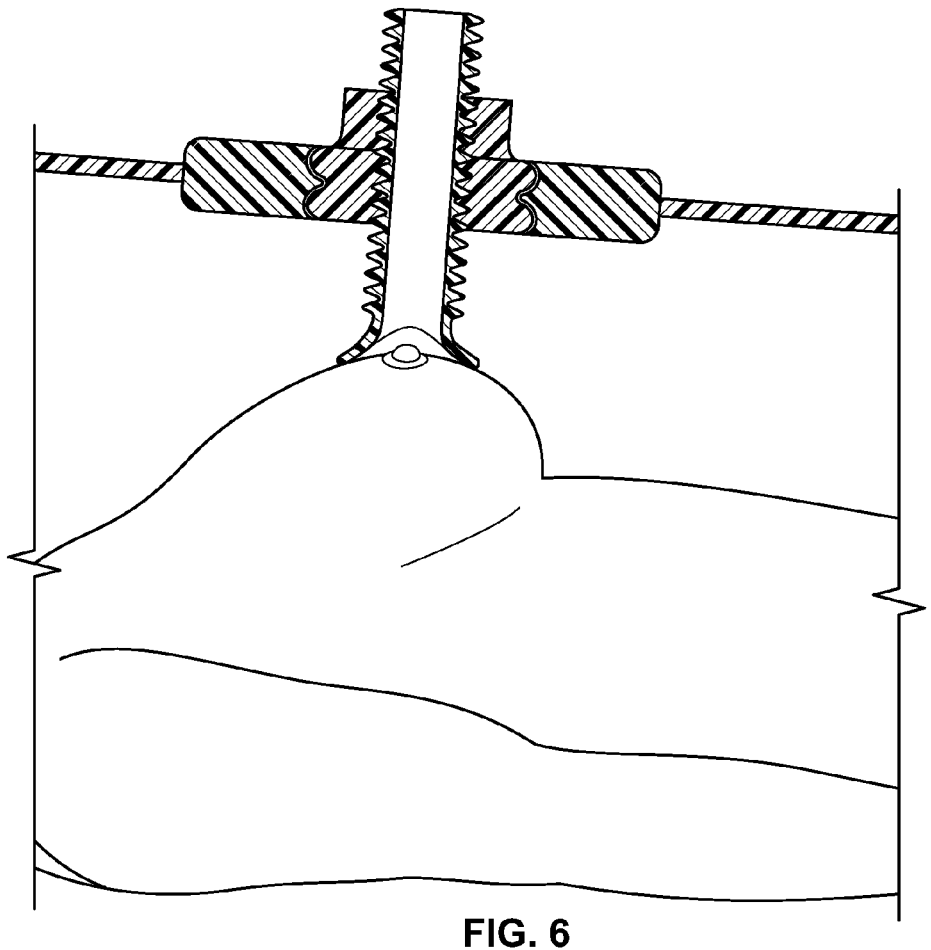
FIG. 6 is a side section, detail view of the embodiment of a vacuum shell apparatus of FIG. 5B, showing a moveable negative pressure point positioned over a breast.
Figure 7A:
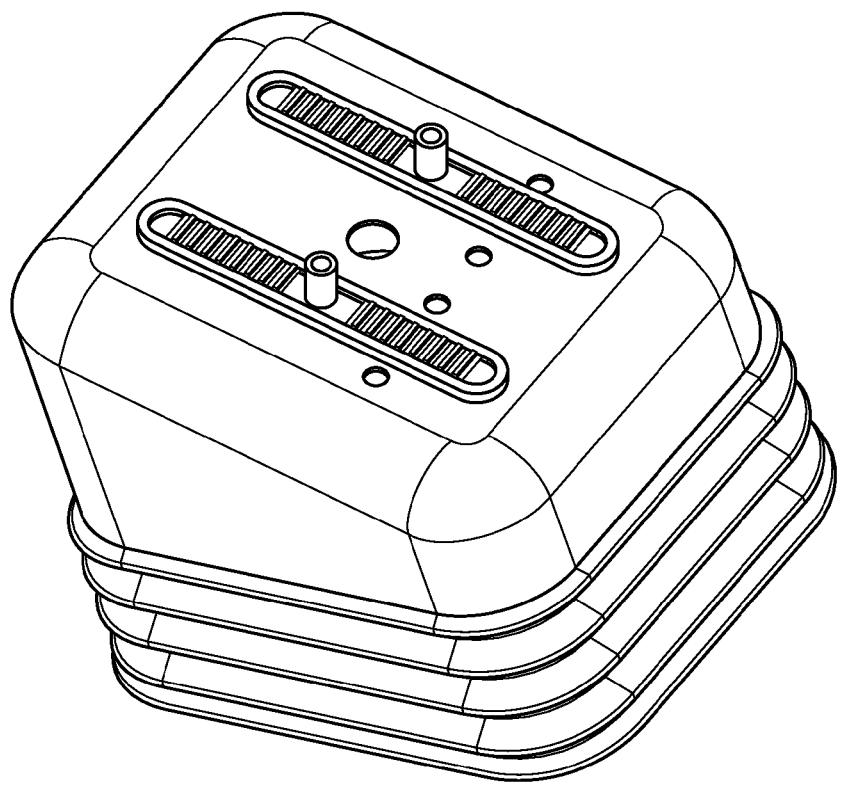
FIG. 7A is a top perspective view of the embodiment of the vacuum shell apparatus of FIG. 5A.
Figure 7B:
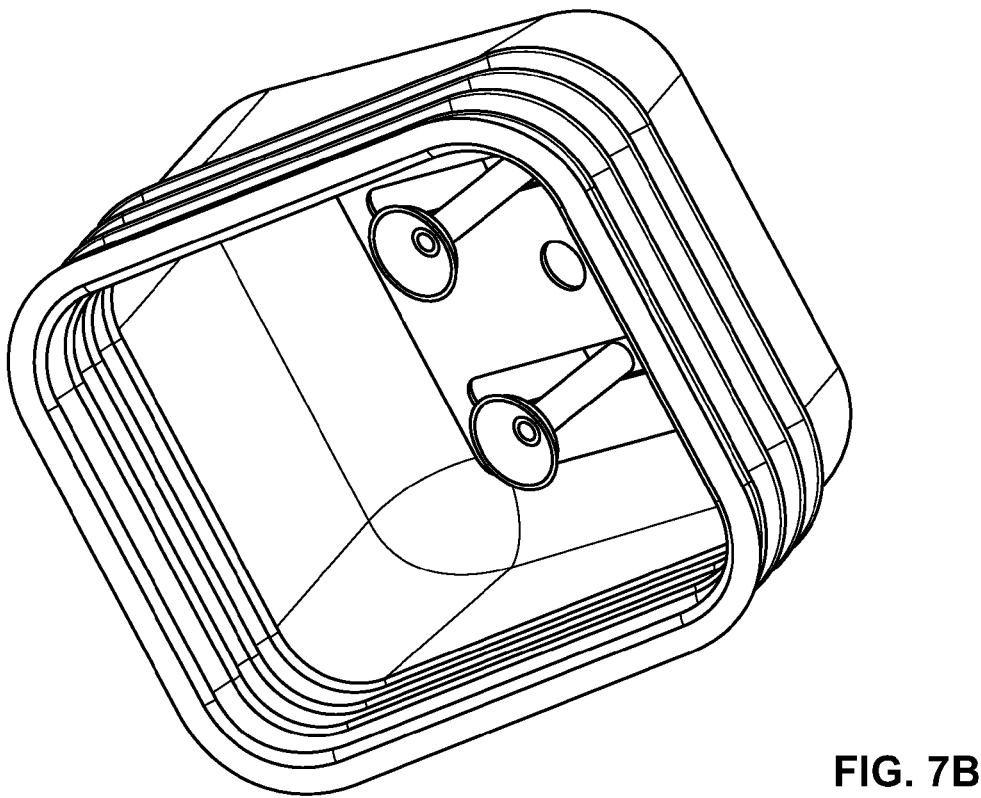
FIG. 7B is a bottom perspective view of the embodiment of a vacuum shell apparatus of FIG. 7A.
Figure 8:
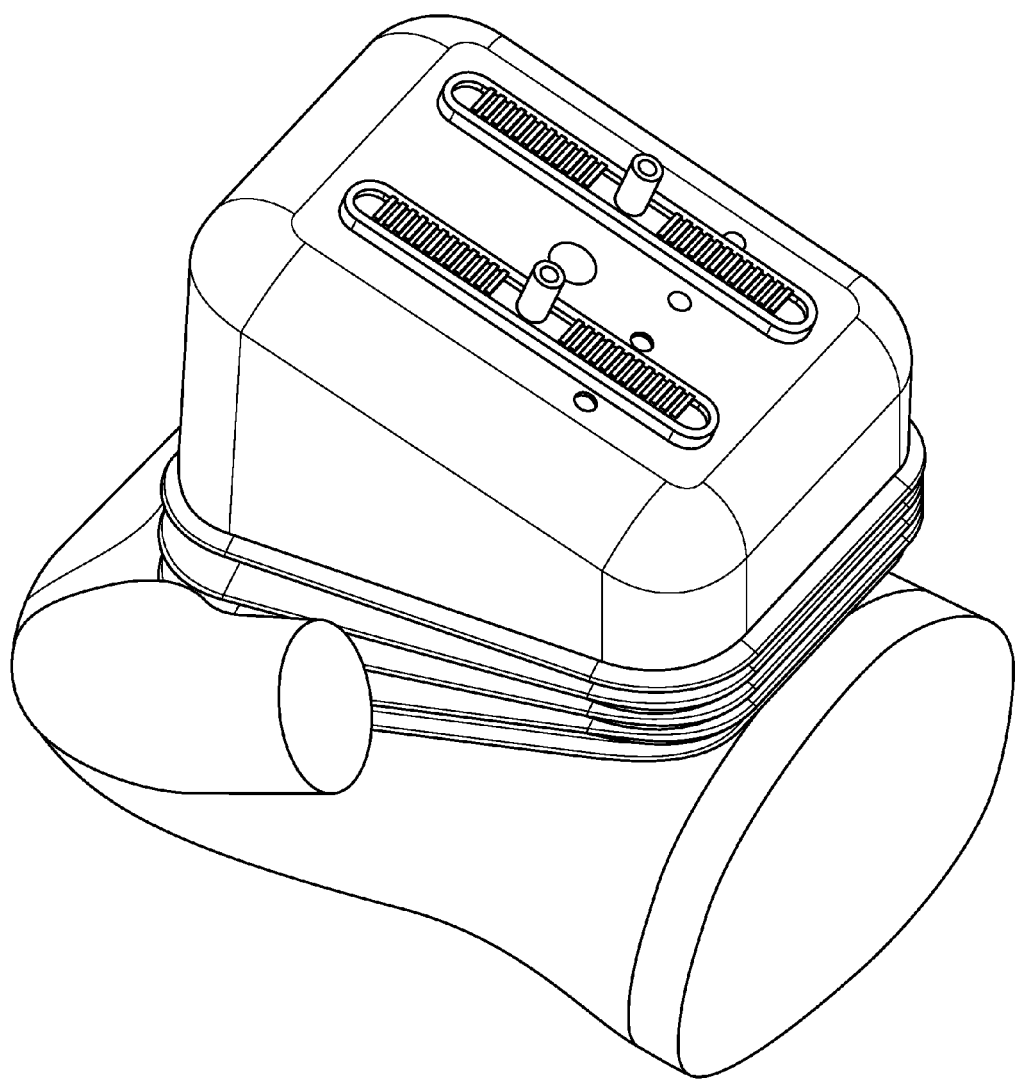
FIG. 8 is a top perspective view of the embodiment of the vacuum shell apparatus of FIG. 7A, showing how it would be mounted in a breast augmentation or other surgical procedure.

A schematic drawing of a vacuum hose assembly 217 is shown at FIG. 4. As shown in FIG. 4, hose assembly 217 comprises cylindrical sleeve 217a having a diameter slightly greater than the slots forming vacuum port 215. The sleeve 217a may have a narrow portion 217b which is the portion that reclosably pierces the sealed slots 215a. The narrow portion 217b has a length approximately equal to the thickness of the shell 212. The sleeve may further comprise a wide end flange 217b that can be detachably connected to the narrow portion 217b, so that the sleeve 217a can be securely mounted to the slots 215a of the vacuum port 215, with the narrow portion 217b piercing the slits 215b. Inside the sleeve a vacuum hose 217 may be sealingly mounted, such that the vacuum hose can travel in the assembly 217 along the slots 215a around the shell 212. As the assembly 217 moves through slots 215a, the portion of the slits 215b that were pierced by narrow portion 217b may reclose as the hose assembly 217 moves to another location. In addition, the hose 217d may be slid through the sleeve 217a to provide allow the hose nearer or further contact with the tissue being operated upon. The hose 217d may have a tab 217e at the end to prevent the hose from being drawn out of the sleeve during operation.

In this manner, the surgeon operating a robotic surgery device can place the shell 212 against the patient, apply negative pressure throughout the shell 212, and provide localized negative pressure to specific areas under the shell 212, to help locally expose the skin and hold soft tissue in place, in the exact location where the surgeon is operating, without requiring extensive manual manipulation of the soft tissue. All this may be done while maintaining negative pressure throughout the shell 212 via the vacuum pump 216.

Referring to FIGS. 5A, 5B, 6, 7A, 7B and 8, an alternative embodiment of vacuum shell apparatus is shown, that provides one or more moveable negative pressure points so that the breast or other soft tissue can be maneuvered to allow for surgeries such as mastectomy and reconstruction to be performed with more accuracy and less scarring.

There are various changes and modifications which may be made to the invention as would be apparent to those skilled in the art without departing from the concept and scope of the invention. While the invention has been described in terms of the preferred embodiment of breast surgery, those of skill in the art will readily appreciate that the apparatus and methods may be adapted to other soft tissue surgery, and that modifications may be made as to the means for adjusting the location of a vacuum within the shell. These changes or modifications are included in the teaching of the disclosure and it is intended that the invention be limited only by the scope of the claims appended hereto.

What is claimed is:

1. A device for expanding and manipulating soft tissue during surgery, comprising:
   a shell capable of withstanding negative pressure;
   a flexible sealing rim disposed around the peripheral edges of the shell for sealing to the skin of a patient to isolate a space between the shell and a surgical area;
   one or more instrument ports for allowing resealable entry of surgical instruments;
   a vacuum port that allows negative pressure to be applied to the space.

2. A device according to claim 1, wherein the vacuum port can be relocated to different positions along the shell to provide concentrated negative pressure to a localized area.

3. A device for expanding and manipulating soft tissue during surgery, comprising:
   a shell capable of withstanding negative pressure;
   a flexible sealing rim disposed around the peripheral edges of the shell for sealing to the skin of a patient to isolate a space between the shell and a surgical area;
   one or more instrument ports for allowing resealable entry of surgical instruments; and
   a vacuum port that allows negative pressure to be applied to the space, the vacuum port comprising a slot in the shell, a sealing material in the slot, a sleeve capable of sliding along the slot, and a hose that can be slid through the sleeve to extend into the space.

4. A device for applying negative pressure to a patient during operation of surgical instruments, comprising:
   a shell having a flexible rim for forming a seal on contact with the skin of the patient;
   an instrument port in the shell, comprising a flexible material for reclosable penetration by a surgical instrument; and a vacuum port for applying negative pressure within the shell;

wherein the shell is configured to leave a space between the shell and the skin of the patient when negative pressure is applied within the shell.

5. The device of claim 4, wherein the space between the shell and the skin of the patient is 1 to 5 inches.

6. The device of claim 4, wherein the shell is made of a clear material.

7. The device of claim 4, wherein the flexible rim comprises a silicone gel gasket.

8. The device of claim 4, wherein the flexible rim comprises a pressure sensitive adhesive for sealing contact with the skin.

9. The device of claim 4, further comprising a vacuum pump in communication with the vacuum port, wherein the vacuum pump is regulatable to maintain a negative pressure at less than 20 mmHg.

10. The device of claim 4, wherein the vacuum port is moveable across the shell.

11. The device of claim 10, wherein the vacuum port applies negative pressure within the entire shell and to a localized area within the shell.

12. The device of claim 10, wherein the vacuum port comprises a slot, a pin slit extending lengthwise along the slot, a flexible material disposed in the slot and sealing the pin slit, and a vacuum hose reclosably piercing the pin slit, wherein the vacuum hose can travel along the slot.

13. The device of claim 12, wherein the flexible material is a gel.

14. The device of claim 12, further comprising a sleeve having a diameter greater than the slot and a narrow portion that reclosably pierces the pin slit, and wherein the vacuum hose is mounted within the sleeve.

15. The device of claim 12, wherein the vacuum hose is slidably mounted within the sleeve, to allow the vacuum hose to be slid near or further from contact with the skin.

* * * * *